United States Patent
Okazoe et al.

(10) Patent No.: US 7,271,229 B2
(45) Date of Patent: Sep. 18, 2007

(54) PROCESSES FOR PRODUCING A FLUOROSULFONYL GROUP-CONTAINING COMPOUND AND A COMPOUND LED FROM THE FLUOROSULFONYL GROUP-CONTAINING COMPOUND

(75) Inventors: Takashi Okazoe, Kanagawa (JP); Atsushi Watakabe, Kanagawa (JP); Masahiro Ito, Kanagawa (JP); Kunio Watanabe, Kanagawa (JP); Takeshi Eriguchi, Kanagawa (JP); Kimiaki Kashiwagi, Kanagawa (JP); Shu-zhong Wang, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 164 days.

(21) Appl. No.: 10/830,140

(22) Filed: Apr. 23, 2004

(65) Prior Publication Data

US 2004/0230018 A1 Nov. 18, 2004

Related U.S. Application Data

(63) Continuation of application No. PCT/JP02/11310, filed on Oct. 30, 2002.

(30) Foreign Application Priority Data

Oct. 30, 2001 (JP) .............................. 2001-332813

(51) Int. Cl.
G08F 228/02 (2006.01)
(52) U.S. Cl. ...................... 526/247; 526/242; 526/243; 526/255; 560/184
(58) Field of Classification Search .............. 526/247, 526/242, 255; 560/184
See application file for complete search history.

(56) References Cited

U.S. PATENT DOCUMENTS 3,282,875 A * 11/1966 Connolly et al. ............ 524/795
5,586,626 A * 12/1996 Dolbear et al. ......... 188/250 B 2004/0230018 A1 11/2004 Okazoe et al.

FOREIGN PATENT DOCUMENTS

| JP | 5-213929 | | 8/1993 |
| JP | 05-213929 | * | 8/1993 |
| JP | 2002-260705 | * | 9/2002 |
| WO | WO 00/56694 | | 9/2000 |
| WO | WO-00/56694 | * | 9/2000 |

OTHER PUBLICATIONS

U.S. Appl. No. 11/311,560, filed Dec. 20, 2005, Watakabe et al.
Supervised by Zen'ichiro Takehara, "Nenryo Denchi Gijutsu to sono Oyo", First Edition, Kabushiki Kaisha Techno Systems, Jan. 30, 2000, pp. 95 to 98.
U.S. Appl. No. 11/244,002, filed Oct. 6, 2005, Watakabe et al.
U.S. Appl. No. 11/166,371, filed Jun. 27, 2005, Watakabe et al.
U.S. Appl. No. 10/830,140, filed Apr. 23, 2004, Okazoe et al.
U.S. Appl. No. 10/442,227, filed May 21, 2003, Ito et al.
U.S. Appl. No. 10/808,274, filed Mar. 25, 2004, Ito et al.
U.S. Appl. No. 11/618,088, filed Dec. 29, 2006, Watakabe et al.

* cited by examiner

*Primary Examiner*—David W. Wu
*Assistant Examiner*—Henry S. Hu
(74) *Attorney, Agent, or Firm*—Oblon, Spivak, McClelland, Maier & Neustadt, P.C.

(57) ABSTRACT

A fluorosulfonyl group-containing compound having a high polymerization reactivity, a process for its production, a sulfonyl group-containing polymerizable monomer led from the sulfonyl group-containing compound, and a polymer obtainable by polymerizing the sulfonyl group-containing polymerizable monomer (3)

-continued
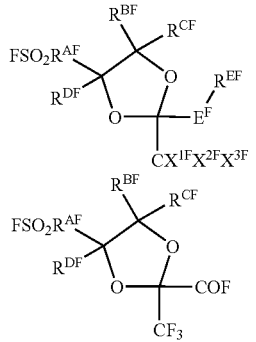
(4)
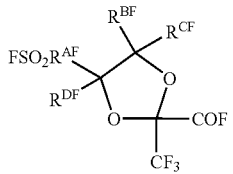
(5-1)
-continued
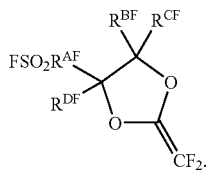
(7-1)
7 Claims, 1 Drawing Sheet F I G. 1
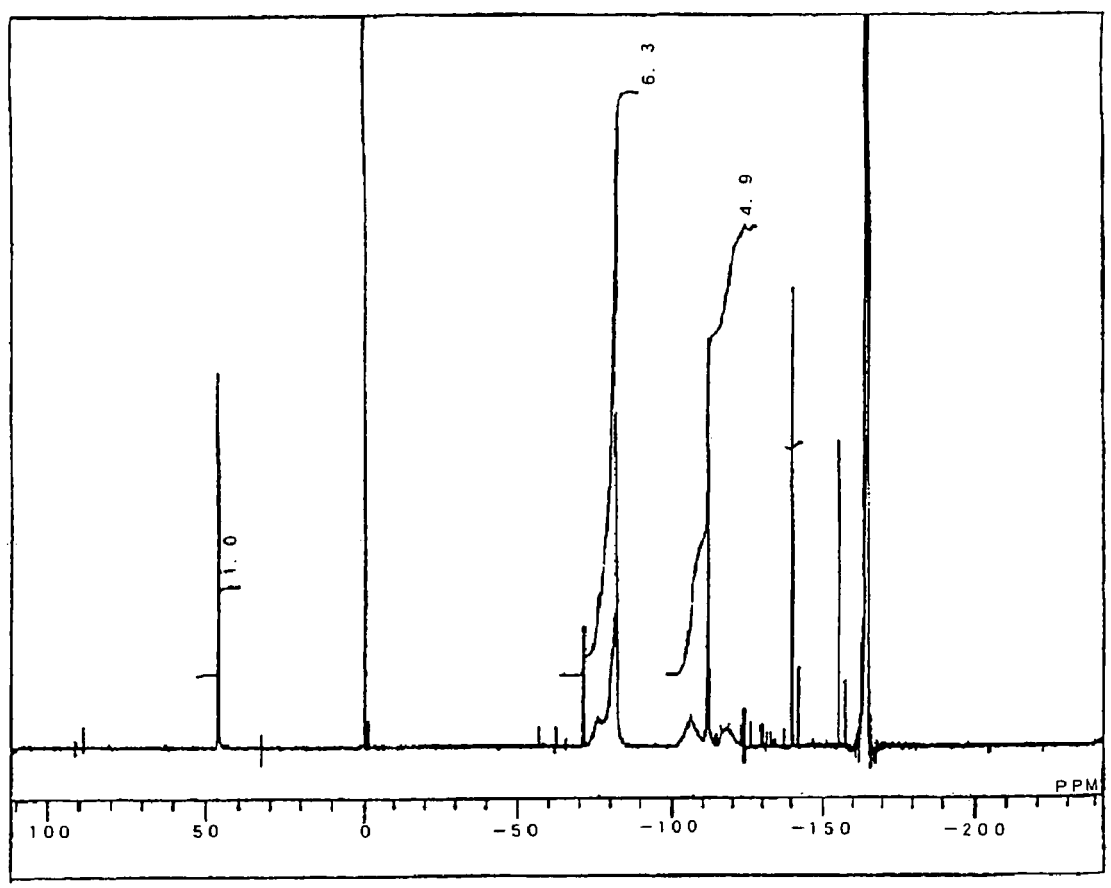

PROCESSES FOR PRODUCING A FLUOROSULFONYL GROUP-CONTAINING COMPOUND AND A COMPOUND LED FROM THE FLUOROSULFONYL GROUP-CONTAINING COMPOUND

TECHNICAL FIELD

The present invention relates to a sulfonic group-containing polymer useful as an ion exchange membrane (such as a membrane to be used for electrolysis of sodium chloride or for a solid polymer type fuel cell) or as an electrolyte to be used for a catalyst layer of a fuel cell, and to processes for producing a polymer containing a fluorosulfonyl group to be used for the production of such a polymer or a fluorosulfonyl group-containing compound useful as a starting material for such a polymer. Further, the present invention relates to a novel compound useful as an intermediate for the production of the sulfonic group-containing polymer.

BACKGROUND ART

Heretofore, a copolymer of tetrafluoroethylene with a fluorinated monomer represented by the following formula, is used for a membrane for electrolysis of sodium chloride or for a membrane or a catalyst layer of a solid polymer type fuel cell. In the following formula, Y is a fluorine atom or a trifluoromethyl group, n is an integer of from 1 to 12, m is an integer of from 0 to 3, p is 0 or 1 and m+p>0.

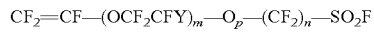

$CF_2=CF-(OCF_2CFY)_m-O_p-(CF_2)_n-SO_2F$

Further, the fluorosulfonyl groups ($-SO_2F$) in the copolymer can be converted to sulfonic groups ($-SO_3H$) by alkali hydrolysis, followed by treatment with an acid.

The sulfonic group-containing polymer (hereinafter sometimes referred to as a sulfonic polymer) is a polymer which is capable of reducing the electric power for electrolysis when used in e.g. an electrolytic cell for sodium chloride in the form of a membrane having a high ion exchange capacity. Further, in a case where such a sulfonic polymer is used for a fuel cell, it is a polymer capable of improving the power generation energy efficiency. And, as such a sulfonic polymer, preferred is a polymer having a larger ion exchange capacity and a lower electric resistance.

However, if it is attempted to increase the ratio of the fluorosulfonyl group-containing monomer to be used for copolymerization for the purpose of increasing the ion exchange capacity of the sulfonic polymer, there has been a problem that the molecular weight of the copolymer tends to be low. A membrane formed of a copolymer having a low molecular weight has had a problem that the mechanical strength and durability are inadequate and as such, is not practically useful.

Further, in the case of a conventional sulfonic monomer, it is required to be copolymerized with tetrafluoroethylene having a high polymerization reactivity in order to obtain a perfluoropolymer having a high molecular weight, and it was impossible to obtain a polymer having a high molecular weight by copolymerization with other perfluoromonomer.

It is an object of the present invention to provide a fluorosulfonyl group-containing compound having a group which can be converted to a sulfonic group and having a high polymerization reactivity and a process for its production, a fluorosulfonyl group-containing polymer having such a compound polymerized, and a sulfonic polymer obtained from such a fluorosulfonyl group-containing polymer.

Further, it is another object of the present invention to provide a fluorosulfonyl group-containing compound having a cyclic structure, which is a monomer satisfying the above object and which has not heretofore been known because of the difficulty in synthesis.

DISCLOSURE OF THE INVENTION

Namely, the present invention provides inventions having the following constructions:

1. A process for producing the following fluorosulfonyl group-containing compound (5), characterized in that the following compound (3) is fluorinated to form the following compound (4), and then, the compound (4) is subjected to a decomposition reaction:

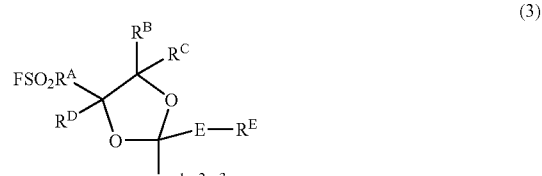

(3)

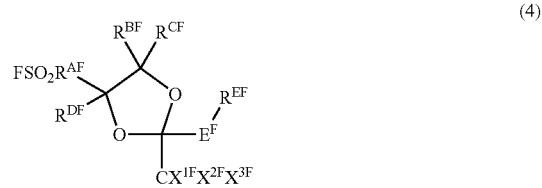

(4)

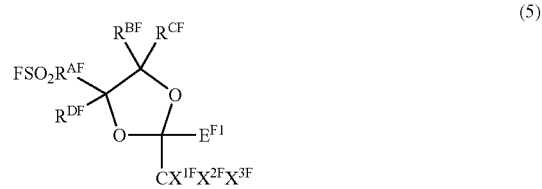

(5)

provided that the symbols in the formulae have the following meanings:

At least one selected from $R^A$ to $R^E$, $X^1$ to $X^3$ and E is a hydrogen atom or a group having hydrogen atom(s), and at least one selected from $R^{AF}$ to $R^{EF}$, $X^{1F}$ to $X^{3F}$ and $E^F$ is a fluorinated group or a fluorine atom;

$R^A$: a bivalent organic group;

$R^{AF}$: a group corresponding to $R^A$, i.e. a bivalent organic group having $R^A$ fluorinated, or the same bivalent organic group as $R^A$;

$R^B$, $R^C$, $R^D$: each independently being a hydrogen atom, a halogen atom or a monovalent organic group;

$R^{BF}$, $R^{CF}$, $R^{DF}$, $R^{BF}$, $R^{CF}$, and $R^{DF}$ are groups which correspond to $R^B$, $R^C$ and $R^D$, respectively; when any one of $R^B$ to $R^D$ is a hydrogen atom, the one of $R^{BF}$ to $R^{DF}$ corresponding to the hydrogen atom is a hydrogen atom or a fluorine atom; when any one of $R^B$ to $R^D$ is a halogen atom, the one of $R^{BF}$ to $R^{DF}$ corresponding to the halogen atom is a halogen atom; when any one of $R^B$ to $R^D$ is a monovalent organic group, the one of $R^{BF}$ to $R^{DF}$ corresponding to the monovalent organic group is a monovalent organic group having the corresponding one of $R^B$ to $R^D$ fluorinated, or the same group as the corresponding one of $R^B$ to $R^D$;

$R^E$: a monovalent organic group;

$R^{EF}$: a group corresponding to $R^E$, i.e. a monovalent organic group having $R^E$ fluorinated, or the same monovalent organic group as $R^E$;

E: a bivalent connecting group;

$E^F$: a group corresponding to E, i.e. the same bivalent connecting group as E, or a bivalent connecting group having E fluorinated;

$E^{F1}$: a group formed by scission of $E^F$;

$X^1$, $X^2$, $X^3$: each independently being a hydrogen atom, a chlorine atom, or a fluorine atom;

$X^{1F}$, $X^{2F}$, $X^{3F}$, $X^{1F}$, $X^{2F}$ and $X^{3F}$ correspond to $X^1$, $X^2$, $X^3$, respectively; when any one of $X^1$ to $X^3$ is a hydrogen atom, the one of $X^{1F}$ to $X^{3F}$ corresponding to the hydrogen atom, is a hydrogen atom or a fluorine atom; when any one of $X^1$ to $X^3$ is a fluorine atom, the one of $X^{1F}$ to $X^{3F}$ corresponding to the fluorine atom, is a fluorine atom; and when any one of $X^1$ to $X^3$ is a chlorine atom, the one of $X^{1F}$ to $X^{3F}$ corresponding to the chlorine atom, is a chlorine atom.

2. The process according to the above 1, wherein the fluorination reaction is carried out by the reaction with fluorine in a liquid phase.

3. The process according to the above 2, wherein the fluorine content of the compound (3) is from 20 to 86 mass %.

4. The process according to the above 2 or 3, wherein the molecular weight of the compound (3) is from 200 to 1,000.

5. The process according to any one of the above 1 to 4, wherein $R^E$ is a perfluorinated monovalent organic group, and $R^{EF}$ is the same group as $R^E$.

6. The process according to any one of the above 1 to 5, wherein the fluorination is a reaction whereby the compound (3) is substantially perfluorinated.

7. The process according to any one of the above 1 to 6, wherein the compound (3) is the following compound (3-1), the compound (4) is the following compound (4-1), and the compound (5) is the following compound (5-1):

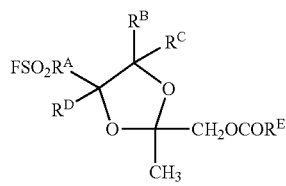
(3-1)

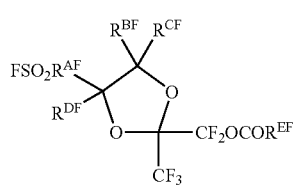
(4-1)

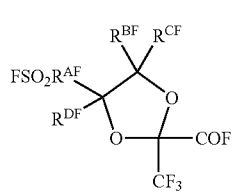
(5-1)

provided that the symbols in the formulae have the same meanings as defined above.

8. The process according to the above 7, wherein the compound (3-1) is a reaction product of the following compound (A1-1) and the following compound (A2-1), a reaction product of the following compound (B1-1) and the following compound (B2-1), or a reaction product obtained by reacting the following compound (C1-1) with acetone to form the following compound (C1-2) and reacting the compound (C1-2) and the following compound (B2-1):

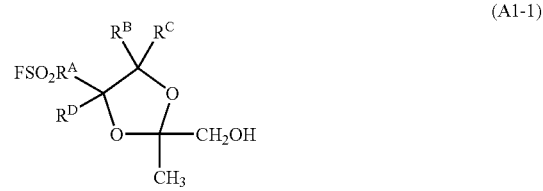
(A1-1)

(A2-1)

$R^E COF$

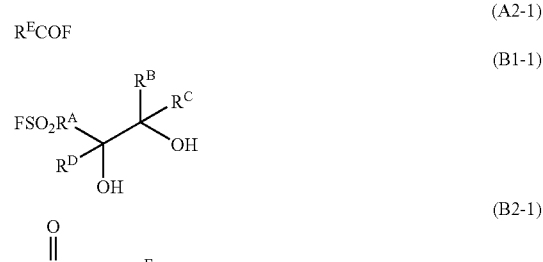
(B1-1)

(B2-1)

$CH_3\overset{O}{\overset{\|}{C}}CH_2OCOR^E$

(C1-1)

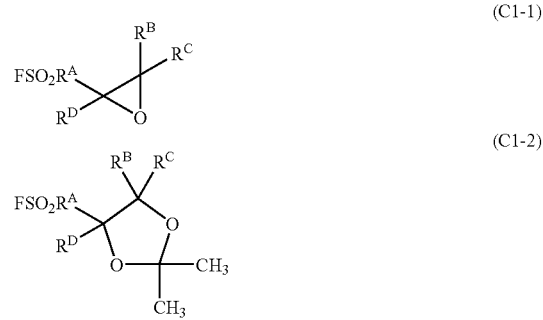
(C1-2)

provided that the symbols in the formulae have the same meanings as defined above.

9. The process according to the above 8, wherein the compound (3-1) is a compound obtained by reacting the compound (C1-1) with acetone to obtain a reaction product containing the compound (C1-2) and acetone, and using the reaction product as it contains the acetone, for the reaction with the compound (B2-1).

10. A process for producing the following compound (7-1), characterized in that the following compound (5-1) is thermally decomposed:

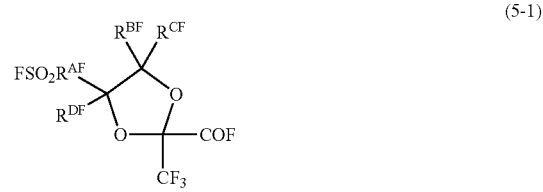
(5-1)

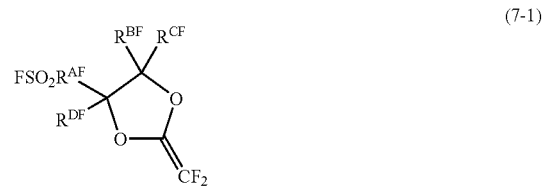
(7-1)

provided that the symbols in the formulae have the same meanings as defined above.

11. A process for producing a fluorosulfonyl group-containing polymer, characterized by polymerizing at least one member of the following compound (7-1), or at least one member of the following compound (7-1) and at least one member of a polymerizable monomer which is copolymerizable with the compound (7-1):

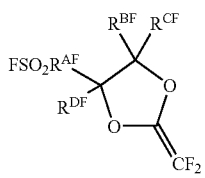
(7-1)

12. A fluorosulfonyl group-containing polymer, comprising monomer units having polymerized at least one member of the following compound (7-1), or monomer units having polymerized at least one member of the following compound (7-1) and monomer units having polymerized at least one member of a polymerizable monomer which is copolymerizable with the compound (7-1):

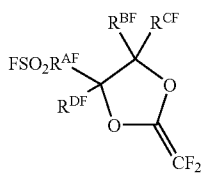
(7-1)

13. The fluorosulfonyl group-containing polymer according to claim 12, which has a molecular weight of from $5\times10^3$ to $5\times10^6$ and contains from 0.1 to 99.9 mol % of the monomer units having polymerized at least one member of a polymerizable monomer which is copolymerizable with the compound (7-1).

14. A process for producing a sulfonate or sulfonic group-containing polymer, characterized in that fluorosulfonyl groups of the fluorosulfonyl group-containing polymer produced by the process of claim 11, are subjected to alkali hydrolysis, or to such alkali hydrolysis, is followed by acid treatment.

15. A fluorosulfonic group-containing polymer comprising monomer units represented by the following formula, or such monomer units and monomer units of another monomer which is copolymerizable with such monomer units:

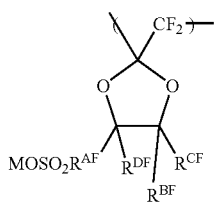

wherein M is a hydrogen atom or a counter ion.

16. The fluorosulfonic group-containing polymer according to claim 15, which has a molecular weight of from $5\times10^3$ to $5\times10^6$ and contains from 0.1 to 99.9 mol % of the monomer units of another copolymerizable monomer.

17. A compound represented by the following formula (7-1A):

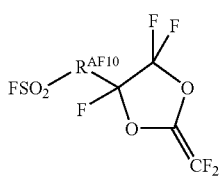
(7-1A)

wherein $R^{AF10}$ is a $C_{1-20}$ perfluoroalkylene group or a $C_{1-20}$ perfluoro(etheric oxygen atom-containing alkylene) group.

18. Any one of the compounds represented by the following formulae, wherein $M^2$ is an alkali metal ion:

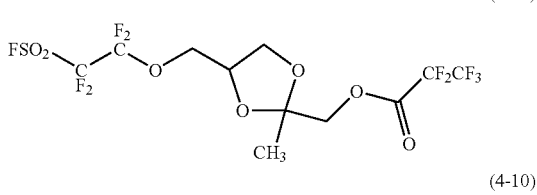
(3-10)

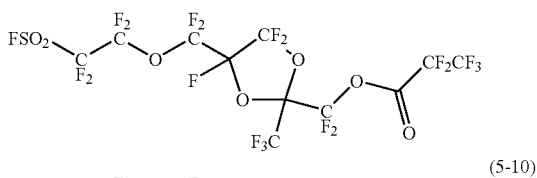
(4-10)

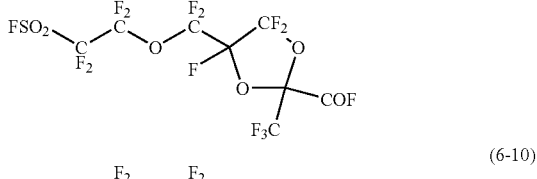
(5-10)

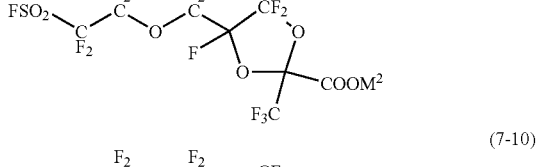
(6-10)

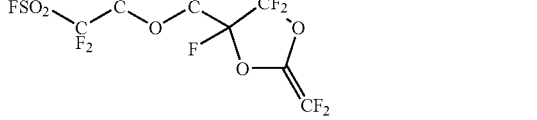
(7-10)

BRIEF DESCRIPTION OF THE DRAWINGS

FIG. 1 is the $^{19}$FNMR spectrum of a homopolymer of the compound (7-10) produced in Example 7 (abscissa: 5 (ppm))

BEST MODE FOR CARRYING OUT THE INVENTION

In this specification, a compound represented by the formula (3) will be referred to as a compound (3). Compounds represented by other formulae will also be likewise referred to.

An organic group is a group having at least one carbon atom. In this specification, such an organic group may be a hydrocarbon group, a halogenated hydrocarbon group, a hetero atom-containing hydrocarbon group or a halogenated (hetero atom-containing hydrocarbon) group. The hydrocarbon group is an organic group comprising a carbon atom and a hydrogen atom. Unless otherwise specified, the carbon number of an organic group is preferably from 1 to 20, more preferably from 1 to 10. The halogenated hydrocarbon group is a hydrocarbon group having at least one hydrogen atom bonded to a carbon atom substituted by a halogen atom. A hetero atom-containing hydrocarbon group is a hydrocarbon group containing a hetero atom (such as an oxygen atom, a nitrogen atom or a sulfur atom) and/or a hetero atomic group (such as —C—C(=O)—C— or —C—SO$_2$—C—). The halogenated (hetero atom-containing hydrocarbon) group is a group having at least one hydrogen atom bonded to a carbon atom in the above hetero atom-containing hydrocarbon group substituted by a halogen atom.

In the compound (3), $R^A$ is preferably a bivalent organic group which can be fluorinated or a bivalent organic group which was perfluorinated. Each of $R^B$ to $R^D$ is preferably a monovalent organic group which can be fluorinated or a hydrogen atom. $R^E$ is preferably a fluorinated monovalent organic group, particularly preferably a perfluorinated monovalent organic group. E is preferably a bivalent organic group containing an ester bond and is preferably such a bivalent organic group which can be fluorinated. $X^1$ to $X^3$ may be the same or different, preferably the same, and more preferably, all are hydrogen atoms.

Specifically, $R^A$ may be a bivalent hydrocarbon group, a hetero atom-containing bivalent hydrocarbon group, a fluoro bivalent hydrocarbon group or a fluoro(hetero atom-containing) bivalent hydrocarbon group, particularly preferably a fluoroalkylene group or a fluoro(etheric oxygen atom-containing alkylene) group. Each of $R^B$ to $R^D$ is preferably a hydrogen atom or an alkyl group, particularly preferably a hydrogen atom. $R^E$ is preferably a fluoro monovalent hydrocarbon group or a fluoro(hetero atom-containing monovalent hydrocarbon) group, particularly preferably a fluoroalkyl group or a fluoro(etheric oxygen atom-containing alkyl) group, especially preferably such a group which is perfluorinated.

E is preferably a group containing an ester bond, particularly preferably —COOCHR$^1$— (wherein the direction of the group is not limited, R$^1$ is a hydrogen atom or a monovalent hydrocarbon group, preferably a hydrogen atom or a methyl group).

The compound (3) is preferably a compound (3) produced by the following method A, B or C.

Method A: A method to obtain a compound (3) by reacting the following compound (A1) and the following compound (A2).

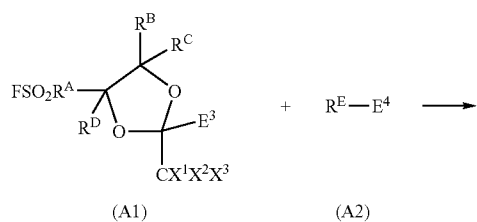

(A1)          (A2)

-continued

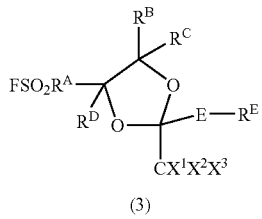

(3)

In the formulae, $R^A$ to $R^E$, $X^1$, $X^2$ and $X^3$ have the same meanings as above, respectively, and their preferred embodiments are also the same as above. $E^3$ and $E^4$ are groups which react with each other to form a bivalent connecting group (E), and it is preferred that one of $E^3$ and $E^4$ is —CHR$^1$OH, and the other is X$^4$CO— (wherein R$^1$ has the same meaning as above, and X$^4$ is a halogen atom, preferably a fluorine atom). —CHR$^1$OH and X$^4$CO— are able to form —CHR$^1$OCO— as the bivalent connecting group (E) by an esterification reaction.

In the method A, when E is an ester bond-containing group (—CHR$^1$OCO—), the compound (3) is preferably the following compound (3-1) from the viewpoint of the usefulness of the desired compound. The compound (3-1) can be obtained as a reaction product of an esterification reaction of the following compound (A1-1) and the compound (A2-1). The symbols in the following formulae have the same meanings as described above.

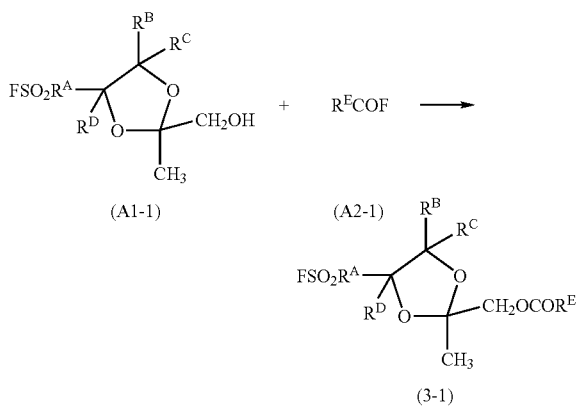

(A1-1)          (A2-1)

(3-1)

The esterification reaction can be carried out under the conditions of a known esterification reaction. Such a reaction may be carried out in the presence of a solvent, but is preferably carried out in the absence of a solvent, in view of the volume efficiency. In a case where a solvent is used, the amount of the solvent is preferably at most 500 mass %, particularly preferably from 50 to 500 mass %, based on the total amount of the compound (A1-1) and the compound (A2-1).

Further, the reaction temperature for the esterification reaction is at least −50° C. and is preferably at most the boiling point of the solvent and at most +100° C. Further, the reaction time for the reaction may optionally be changed depending upon the supply rate of the starting materials and the amount of compounds to be used for the reaction, and the reaction pressure (gauge pressure, the same applies hereinafter) is preferably from atmospheric pressure to 2 MPa.

In the reaction of the compound (A1-1) and the compound (A2-1), HF will be generated. To neutralize this HF, a neutralizing agent such as an alkali metal fluoride (preferably NaF or KF) or a trialkylamine, may be present in the reaction system. In a case where such a neutralizing agent is not used, it is preferred that the acid is discharged out of the reaction system as carried by an inert gas stream (such as a nitrogen gas stream). In a case where an alkali metal fluoride is employed, the amount is preferably from 1 to 10 times by mol, relative to the compound (A2-1).

Method B:

A method of obtaining a compound (3) by reacting the following compound (B1-1) and the following compound (B2). The symbols in the formulae have the same meanings as described above.

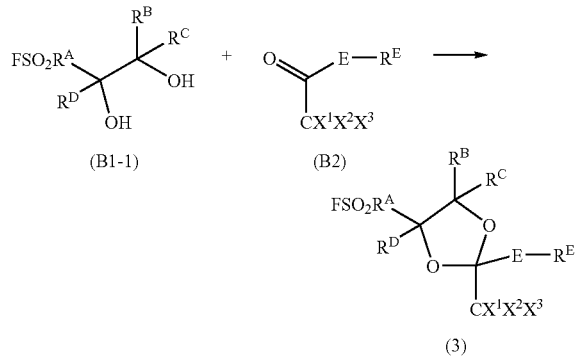

As a specific example of the method B, a method for producing a compound (3-1) by a reaction of the following compound (B1-1) and the compound (B2-1), may be mentioned. The symbols in the following formulae, have the same meanings as described above.

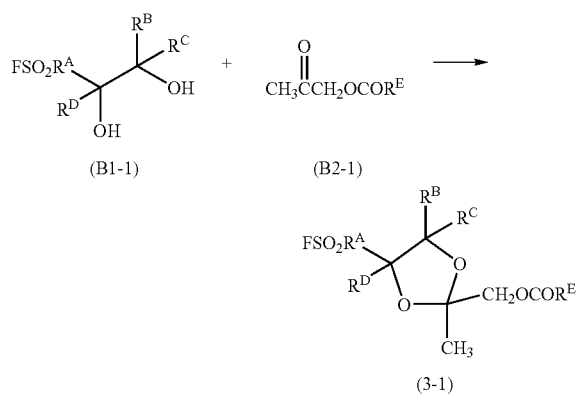

The reaction of the compound (B1-1) and the compound (B2-1) is preferably carried out in the presence of an acid catalyst and an orthoformate or an orthoacetate.

The acid catalyst may, for example, be a liquid inorganic acid such as hydrochloric acid or sulfonic acid, a Lewis acid such as titanium tetrachloride, boron trifluoride etherate, aluminum chloride or zinc chloride or a solid acid catalyst such as a perfluorosulfonate polymer, such a polymer in a beads form or a porous nanocomposite having such a polymer supported on amorphous silica. Among them, a solid acid catalyst is preferred from such a viewpoint that separation from the formed product is easy.

As the orthoformate or the orthoacetate, a methyl ester or an ethyl ester is preferred in due of availability. The reaction temperature for the reaction is preferably at least −10° C. and is particularly preferably at most the boiling point of the compound having the lowest boiling point among the compounds to be used for the reaction.

The compound (B1-1) can be prepared by reacting the following compound (C1-1) with water in the presence of an acid catalyst. As the compound (B1-1), the following compound (B1-10) is preferred.

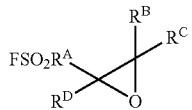

$$FSO_2(CF_2)_2OCH_2CH(OH)CH_2OH \quad (B1\text{-}10)$$

This compound (B1-10) can be produced by a method disclosed in J. Fluorine Chem., Vol. 46, 39 (1990) and J. Fluorine Chem., Vol. 68, 253 (1994), or by a method which will be described in the method C. As an example of the production route for the compound (B1-1), the following example may be mentioned.

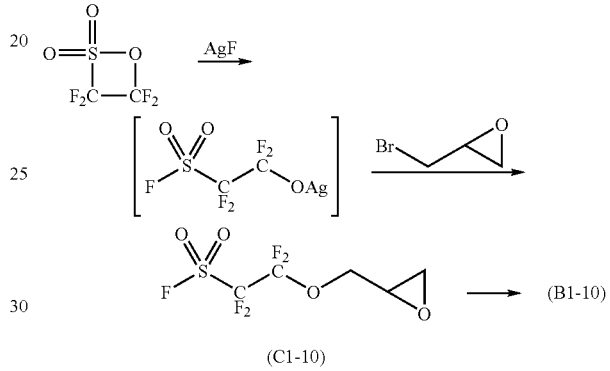

The compound (B2-1) is preferably produced by an esterification reaction of the following compound (B2-a) with the compound (B2-b), wherein $X^4$ is a hydroxyl group or a halogen atom.

$$CH_3CO-CH_2OH \quad (B2\text{-}a)$$

$$X^4COR^E \quad (B2\text{-}b)$$

Method C:

A method for obtaining a compound (3) by reacting the following compound (C1-2) and the following compound (B2). The symbols in the formulae have the same meanings as described above.

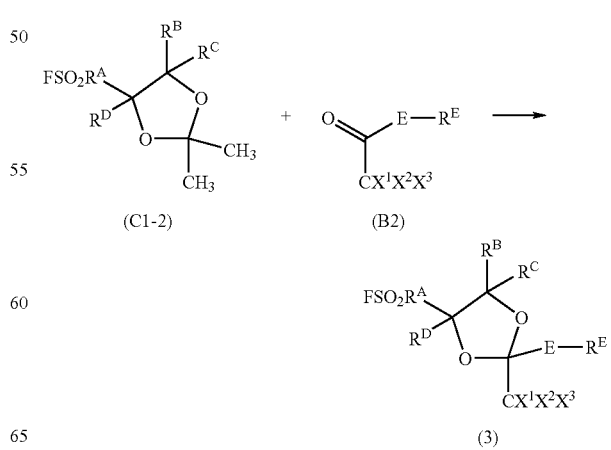

As a specific example of the method C, a method for producing a compound (3-1) by a reaction of the following compound (C1-2) with the compound (B2-1). The symbols in the following formulae have the same meanings as described above.

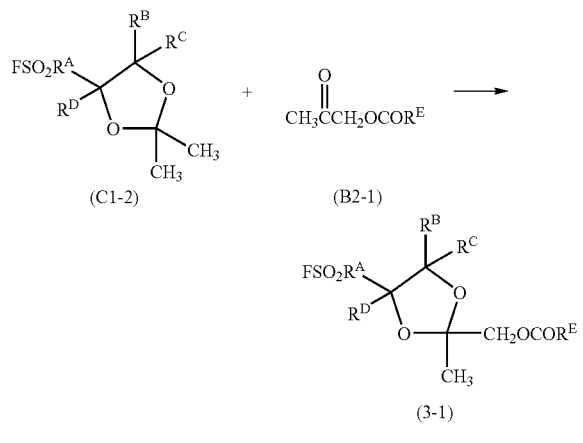

(C1-2)    (B2-1)

(3-1)

As the compound (C1-2), the following compound (C1-20) is preferred.

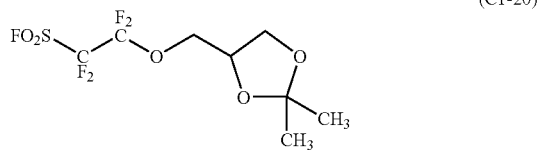

(C1-20)

The reaction of the compound (C1-2) and the compound (B2-1) is preferably carried out in the presence of an acid catalyst. As an acid catalyst, the same one as described with respect to the method B may be employed, and a Lewis acid catalyst such as titanium tetrachloride, boron trifluoride etherate, aluminum chloride or zinc chloride, is preferred.

The temperature for the reaction of the compound (C1-2) and the compound (B2-1) is preferably from 0 to 180° C., particularly preferably from room temperature to 120° C. Further, it is preferred to carry out the reaction while removing acetone formed as a by-product by the reaction from the reaction system, by a method such as distillation, whereby the compound (3-1) can be obtained in good yield in a short period of time. Further, it is particularly preferred that at the time of removing acetone, a solvent having a higher boiling point than acetone is added and heated, preferably heated under reduced pressure, whereby acetone can be more efficiently removed. As a specific example of the solvent having such a high boiling point, benzene, toluene, xylene, hexane, heptane, octane, nonane, decane, undecane, dodecane, chlorobenzene, dichlorobenzene, chloroform, dichloroethane or ethyl acetate may, for example, be mentioned, and particularly preferred is toluene.

As a method for producing the compound (C1-2) as the starting material for the method C, a method by a reaction of the above compound (B1-1) with acetone, or a method by a reaction of the following compound (C1-1) with acetone, may be mentioned. The latter method is preferred. Particularly, the compound (C1-20) as a preferred embodiment of the compound (C1-2), is preferably produced by a reaction of the above compound (C1-10) with acetone.

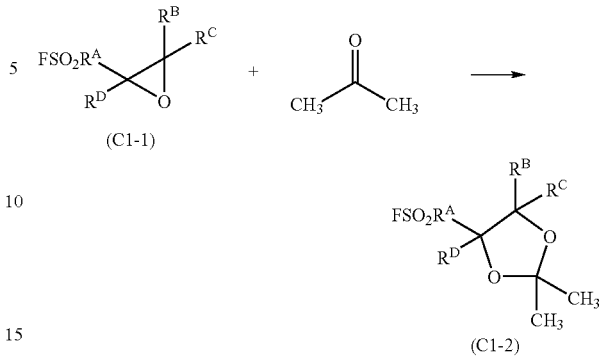

(C1-1)

(C1-2)

As an example of the method for producing the compound (C1-1) as the starting material of the latter method, a method of oxidizing the following compound (D-1) with an oxidizing agent, may be mentioned. As an example of the oxidizing agent, m-chloroperbenzoic acid, a perbenzoic acid, a peracetic acid, or hydrogen peroxide, may, for example, be mentioned.

(D-1)

The compound (C1-10) as a preferred embodiment of the compound (C1-1), can be produced by the production route as described in the explanation of the method B. However, it can also be obtained by preparing the following compound (D-10) by the following method as disclosed in J. Fluorine Chemistry Vol. 46, 21-38 (1990), and oxidizing the compound (D-10) by means of an oxidizing agent. As an example of the metal fluoride ($M^3F$) in the following formulae, KF, $C_sF$ or $A_gF$ may be mentioned.

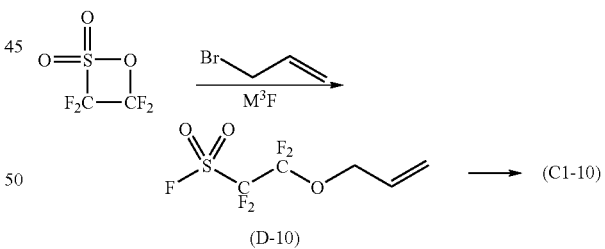

(D-10)    (C1-10)

The reaction of the compound (C1-1) and acetone is preferably carried out in the presence of an acid catalyst. As such an acid catalyst, the same one as used for the reaction of the compound (C1-2) and the compound (B2-1), may be employed, and the preferred embodiments are also the same.

The compound (C1-2) obtained by the above method employing acetone, may be, after isolating by removing acetone and, if necessary, carrying out purification, reacted with the compound (B2-1). Otherwise, the compound (C1-2) obtained by the reaction of the compound (C1-1) and acetone, may be, in the form of a product containing acetone, used for the reaction with the compound (B2-1), and the reaction may be carried out while removing acetone.

In a case where the compound (C1-1) is used as a starting material, the latter method is advantageous in that the process is shorter than the method B, and it is suitable for mass production.

In the present invention, the compound (3) is fluorinated to obtain a compound (4). The compound (3) is preferably a compound which is readily soluble in a liquid phase when the after-mentioned liquid phase fluorination is carried out, and which has an adequate molecular weight to prevent a decomposition reaction. Namely, the molecular weight of the compound (3) is preferably from 200 to 5000, particularly preferably from 200 to 1000. If the molecular weight is too small, particularly when it is less than 200, the compound (3) tends to be readily evaporated, whereby a decomposition reaction in the gas phase is likely to take place at the time of the liquid phase fluorination. On the other hand, if the molecular weight is too large, especially when it exceeds 1000, purification of the compound (3) is likely to be difficult.

Further, the compound (3) in a case where the liquid phase fluorination is carried out, is preferably such that the fluorine content is at least 20 mass %, more preferably from 20 to 86 mass %, still preferably from 20 to 76 mass %. And, in order to obtain such a fluorine content, it is preferred to suitably change the respective groups in the compound (3), particularly the structure of the group ($R^E$).

$R^E$ in the compound (3) is as described above, and the carbon number of $R^E$ is preferably from 2 to 20, particularly preferably from 2 to 10. The following examples may be mentioned as specific examples of $R^E$.

$CF_3CF_2$—,
$CF_3(CF_2)_2OCF(CF_3)$—,
$CF_3(CF_2)_2OCF(CF_3)CF_2OCF(CF_3)$—,
$(CF_3)_2CF$—,
$CF_3CF_2CF(CF_3)$—,

Further, it is preferred that $R^E$ is the following group, whereby in a case where the after-mentioned decomposition reaction of the compound (4) is a decomposition reaction of an ester bond, the compound (5-1) and the compound (6-1) being the products of the decomposition reaction, will be the same compounds.

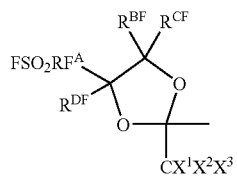

The compound (3) in the present invention is preferably purified before carrying out the fluorination reaction so as to let the fluorination reaction proceed smoothly. Especially when the compound (3-1) is produced by the above-mentioned method A or B, it is preferably purified prior to the fluorination reaction, so that the remaining amount of the unreacted compound having a hydroxyl group can be minimized. As the purification method, a distillation method, a method of treatment with a dilute alkaline aqueous solution for liquid separation, a method of extraction with an organic solvent, followed by distillation, or a silica gel column chromatography, may, for example, be mentioned.

As a method for the fluorination reaction, a fluorination reaction carried out in a liquid phase such as an electrolytic fluorination method (ECF method), a cobalt fluorination method, or a method of reacting with fluorine in a gas phase, may be mentioned. However, from the viewpoint of the operation efficiency and the yield of the reaction, fluorination carried out in a liquid phase is especially advantageous. Particularly preferred is a method of reacting the compound (3) with fluorine ($F_2$) in a liquid phase (a method so-called liquid phase fluorination).

In the liquid phase fluorination, as the fluorine, fluorine gas may be used as it is or fluorine gas diluted with an inert gas may be employed. As such an inert gas, nitrogen gas or helium gas is preferred, and from the economical reason, nitrogen gas is particularly preferred. The amount of fluorine in the nitrogen gas is not particularly limited, and from the viewpoint of efficiency, it is preferably made to be at least 10 vol %, particularly preferably at least 20 vol %.

In the liquid phase fluorination, in order to form a liquid phase, a solvent is usually employed. As such a solvent, a solvent which essentially contains a C—F bond and which contains no C—H bond, is preferred. Further, a perfluoroalkane or an organic solvent prepared by perfluorinating a known organic solvent having at least one atoms selected from the group consisting of a chlorine atom, a nitrogen atom, and an oxygen atom in its structure, is preferred. Further, as such a solvent, a solvent presenting a high solubility to the compound (3) is preferred, and it is particularly preferred to employ a solvent capable of dissolving at least 1 mass %, particularly at least 5 mass %, of the compound (3).

Examples of such a solvent include the compound (4) in a case where it is a perfluorinated compound, the compound (5) in a case where it is a perfluorinated compound, and the following compound (6) in a case where it is a perfluorinated compound, a perfluoroalkane (trade name: FC-72, etc.), a perfluoroether (FC-75, FC-77, etc.), a perfluoropolyether (trade name: KRYTOX, FOMBLIN, GALDEN, DEMNUM, etc.), a chlorofluorocarbon (trade name: FLON LUBE), a chlorofluoropolyether, a perfluoroalkylamine (such as a perfluorotrialkylamine), and an inert fluid (trade name: FLUORINERT). From such a merit that workup after the reaction is easy, the solvent is preferably at least one member selected from the compound (4) in a case where it is a perfluorinated compound, the compound (5) in a case where it is a perfluorinated compound, and the following compound (6) in a case where it is a perfluorinated compound. Further, the amount of the solvent is preferably at least 5 times by mass, particularly preferably from 10 to 100 times by mass, to the compound (3).

The reaction system for the liquid phase fluorination reaction may be a batch system or a continuous system. Further, the liquid phase fluorination reaction is preferably carried out by the following fluorination method 1 or 2, and from the viewpoint of the yield and selectivity of the reaction, it is preferably carried out by the fluorination method 2. As the fluorine gas, one diluted with an inert gas such as nitrogen gas may be used in a case where the reaction is carried out by a batch system or in a case where it is carried out by a continuous system.

Fluorination Method 1

A method wherein the compound (3) and a solvent are charged into a reactor, stirring is initiated, and the reaction temperature and pressure are controlled to prescribed levels, whereupon the reaction is carried out while continuously supplying fluorine gas, or fluorine gas and the solvent.

Fluorination Method 2

A method wherein a solvent is charged into a reactor, stirring is initiated, and the reaction temperature and pressure are controlled to prescribed levels, whereupon fluorine gas and the compound (3) are continuously and simultaneously supplied in a prescribed molar ratio.

In the fluorination method 2, when the compound (3) is supplied, it is preferred to supply the compound (3) diluted with a solvent, whereby the selectivity can be improved, and the amount of by-products can be suppressed. Further, in the fluorination method 2, when the compound (3) is to be diluted with the solvent, the amount of the solvent to the compound (3) is preferably set to be at least 5 times by mass, particularly preferably at least 10 times by mass.

The amount of fluorine to be used for the liquid phase fluorination is preferably set to be such an amount that the fluorine amount is always in excess equivalent to the hydrogen atoms to be fluorinated, particularly preferably set to be such an amount that it is at least 1.5 times by equivalent (i.e. at least 1.5 mols) to such hydrogen atoms, from the viewpoint of the selectivity, either in a case where the reaction is carried out by a batch system or in a case where it is carried out by a continuous system. Further, the fluorine amount is preferably maintained to be always in excess equivalent from the initiation of the reaction to the end of the reaction.

The reaction temperature for the liquid phase fluorination is usually preferably at least −60° C. and at most the boiling point of the compound (3), and from the viewpoint of the reaction yield, selectivity and industrial operation efficiency, it is particularly preferably from −50° C. to +100° C., especially preferably from −20° C. to +50° C. The reaction pressure for the liquid phase fluorination is not particularly limited, and it is particularly preferably from atmospheric pressure to 2 MPa from the viewpoint of the reaction yield, selectivity and industrial operation efficiency.

Further, in order to let the liquid phase fluorination proceed efficiently, it is preferred to add a C—H bond-containing compound to the reaction system at a later stage of the reaction, or to carry out ultraviolet irradiation. By the use of the C—H bond-containing compound, the compound (3) present in the reaction system can efficiently be fluorinated, whereby the reactivity can remarkably be improved.

The C—H bond-containing compound is an organic compound other than the compound (3), and is particularly preferably an aromatic hydrocarbon, especially preferably benzene, toluene, etc. The amount of the C—H bond-containing compound to be added, is preferably from 0.1 to 10 mol %, particularly preferably from 0.1 to 5 mol %, to hydrogen atoms in the compound (3).

The C—H bond-containing compound is preferably added in a state where fluorine gas is present in the reaction system. Further, in a case where the C—H bond-containing compound is added, it is preferred to pressurize the reaction system. The pressure during the pressurizing is preferably from 0.01 to 5 MPa.

By the fluorination reaction in the present invention, the compound (3) is fluorinated to form a compound (4). In the compound (4), $R^{AF}$ to $R^{EF}$, $E^F$ and $X^{1F}$ to $X^{3F}$ are groups which correspond to $R^A$ to $R^E$, E and $X^1$ to $X^3$, respectively. In a case where the groups in the compound (3) are respectively groups which can be fluorinated and they are actually fluorinated, the groups in the compound (4) are groups having the respective corresponding groups fluorinated. However, even if the groups in the compound (3) are groups which can be fluorinated if they were not fluorinated, or if the groups in the compound (3) are groups which can not be fluorinated, the groups in the compound (4) will be the same groups corresponding to the respective groups. However, at least one selected from $R^A$ to $R^E$, $X^1$ to $X^3$ and E is a group having hydrogen atom(s) or a hydrogen atom, and at least one selected from $R^{AF}$ to $R^{EF}$, $X^{1F}$ to $X^{3F}$ and $E^F$ in the compound (4) is a group or atom formed by fluorination.

In the fluorination reaction in the present invention, hydrogen atom(s) bonded to carbon atom(s) will be substituted by fluorine atom(s), but a chlorine atom, a bromine atom or an iodine atom bonded to a carbon atom will not be substituted by a fluorine atom.

In a case where $R^A$ to $R^E$ in the compound (3) are organic groups, if such organic groups are not fluorinated, or if such organic groups are perhalogenated organic groups (such as perfluorinated organic groups), $R^{AF}$ to $R^{EF}$ are the same groups as the corresponding $R^A$ to $R^E$, respectively. On the other hand, in a case where $R^A$ to $R^E$ are organic groups which can be fluorinated, and if they are fluorinated, $R^{AF}$ to $R^{EF}$ will be organic groups having the corresponding R to $R_E$ fluorinated, respectively. In a case where $R^A$ to R are hydrogen atoms, if they are fluorinated, $R^{AF}$ to $R^{EF}$ are fluorine atoms. In a case where $R^A$ to $R^E$ are hydrogen atoms, if they are not fluorinated, $R^{AF}$ to $R^{EF}$ will be hydrogen atoms, respectively. In a case where $R^A$ to $R^E$ are halogen atoms, $R^{AF}$ to $R^{EF}$ will be the halogen atoms. In a case where $X^1$ to $X^3$ are hydrogen atoms, if they are fluorinated, $X^{1F}$ to $X^{3F}$ will be fluorine atoms, and in a case where $X^1$ to $X^3$ are hydrogen atoms, if they are not fluorinated, $X^{1F}$ to $X^{3F}$ will be hydrogen atoms. In a case where $X^1$ to $X^3$ are chlorine atoms or fluorine atoms, $X^{1F}$ to $X^{3F}$ will be the same chlorine atoms or fluorine atoms as the corresponding $X^1$ to $X^3$.

In a case where E in the compound (3) is a bivalent connecting group which is not fluorinated or a bivalent connecting group which can be fluorinated but is not fluorinated, $E^F$ will be the same bivalent connecting group as E. Even if E is a bivalent connecting group which can be fluorinated and is fluorinated, $E^F$ will be a bivalent connecting group having E fluorinated.

As the compound (4) obtained by fluorinating the compound (3), preferred is a compound having the structures which can be fluorinated in the compound (3), substantially perfluorinated. Here, "substantially perfluorinated" means that even if a part of the structures which can be fluorinated in the compound (3) is not fluorinated, the nature as the compound is fluorinated to such an extent equal to the completely fluorinated compound (3). The compound (4) is preferably a compound wherein the structures which can be fluorinated in the compound (3), are completely fluorinated (i.e. perfluorinated).

Specifically, it is preferred that $R^A$ is a bivalent organic group which can be fluorinated, or a bivalent organic group which is perfluorinated, and $R^{AF}$ is a perfluorinated bivalent organic group. It is preferred that each of $R^B$ to $R^D$ is a monovalent organic group which can be fluorinated, or a hydrogen atom, and each of $R^{BF}$ to $R^{DF}$ is preferably a perfluorinated monovalent organic group or a fluorine atom. $R^E$ is preferably a fluorinated monovalent organic group, and $R^{EF}$ is preferably a perfluorinated monovalent organic group. It is preferred that E is —COOCHR$^1$— (wherein R$^1$ has the same meaning as above), and $E^F$ is —COOCFR$^{1F}$— (wherein R$^{1F}$ is a fluorine atom or a perfluorinated monovalent hydrocarbon group, preferably a fluorine atom or a trifluoromethyl group). It is preferred that each of $X^1$ to $X^3$ is a hydrogen atom, and each of $X^{1F}$ to $X^{3F}$ is a fluorine atom.

Particularly, $R^{AF}$ is preferably a perfluoro bivalent hydrocarbon group or a perfluoro(hetero atom-containing bivalent hydrocarbon) group, particularly preferably a perfluoroalkylene group or a perfluoro(etheric oxygen atom-containing alkylene) group. Further, $R^{AF}$ is preferably a $C_{1-20}$ perfluoroalkylene group or a $C_{1-20}$ perfluoro(etheric oxygen atom-containing alkylene) group (such a group having one carbon number is a perfluorooxymethylene group), particularly preferably such a group having from 1 to 12 carbon atoms, especially preferably such a group having from 1 to 6 carbon atoms.

Each of $R^{BF}$ to $R^{DF}$ is preferably a perfluoro monovalent organic group or a fluorine atom, particularly preferably a perfluoroalkyl group or a fluorine atom, especially preferably a fluorine atom or a trifluoromethyl group. $R^{EF}$ is preferably a perfluoro monovalent hydrocarbon group or a perfluoro(hetero atom-containing) monovalent hydrocarbon group, particularly preferably a perfluoroalkyl group or a perfluoro(etheric oxygen atom-containing alkyl) group. Further, $R^{EF}$ is preferably the same group as $R^E$ and is a perfluorinated monovalent organic group.

The bivalent connecting group ($E^F$) is preferably —COOCFR$^{1F}$— (wherein $R^{1F}$ as the same meaning as above) which is formed by fluorination of a bivalent connecting group (E) which is —COOCHR$^1$—.

In the reaction for fluorinating the compound (3) in a liquid phase, it is common that a hydrogen atom is substituted by a fluorine atom to form HF as a by-product. To remove such a by-product HF, it is preferred to incorporate an agent for capturing HF in the reaction system or to contact the discharge gas with a HF capturing agent at the gas outlet of the reactor. As such a HF capturing agent, the same one as the above-mentioned neutralizing agent may be employed, and NaF is preferred.

In the case where a HF capturing agent is incorporated in the reaction system, the amount is preferably from 1 to 20 times by mol, particularly preferably from 1 to 5 times by mol, to the total amount of hydrogen atoms present in the compound (3). In a case where the HF capturing agent is disposed at the gas outlet of the reactor, it is preferred that (a) a cooler (which is preferably maintained at a temperature of from 10° C. to room temperature, particularly preferably at about 20° C.) (b) a NaF pellets-packed layer and (c) a cooler (which is preferably maintained at a temperature of from −78° C. to +10° C., more preferably from −30° C. to 0° C.) are disposed in series in the order of (a)-(b)-(c). Further, a liquid returning line may be installed to return a condensed liquid from the cooler of (c) to the reactor.

The crude product containing the compound (4) obtained in the fluorination step may be used as it is, for the next decomposition reaction, or may be purified to obtain one having a high purity. As such a purification method, a method of distilling the crude product as it is under atmospheric pressure or under reduced pressure, may, for example, be mentioned. The compound (4) is preferably a compound (4-1) formed by fluorination of the compound (3-1).

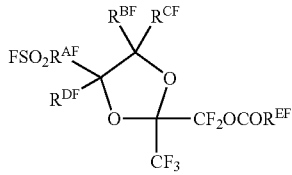
(4-1)

Then, in the present invention, the bivalent connecting group ($E^F$) in the compound (4) is decomposed to obtain the compound (5). This will be described with reference to a case where $E^F$ is —COOCFR$^1$—. The decomposition reaction in the case where $E^F$ is —COOCFR$^1$—, is a decomposition reaction of the ester bond. The decomposition reaction of the ester bond is preferably carried out by a decomposition reaction by heat or by a decomposition reaction carried out in a liquid phase in the presence of a nucleophilic or electrophilic agent.

The decomposition reaction by heat can be carried out by heating the compound (4). The reaction system for the decomposition reaction by heat is preferably selected from the boiling point and the stability of the compound (4). For example, in a case where a readily volatile compound (4) is subjected to heat decomposition, it is possible to employ a gas phase heat decomposition reaction wherein decomposition is continuously carried out in a gas phase, and the discharge gas containing the resulting compound (5) is condensed and recovered.

The reaction temperature for the gas phase heat decomposition reaction is preferably from 50 to 350° C., particularly preferably from 50 to 300° C., especially preferably from 150 to 250° C. Further, an inert gas which is not directly concerned with the reaction, may be co-present in the reaction system. As such an inert gas, nitrogen or carbon dioxide may, for example, be mentioned. The inert gas is preferably added in an amount of from 0.01 to 50 vol % to the compound (4). If the amount of the inert gas to be added, is large, the recovery rate of the product may sometimes decrease.

On the other hand, in a case where the compound (4) is a hardly volatile compound, it is preferred to employ a liquid phase heat decomposition reaction wherein it is heated in the form of a liquid in the reactor. In such a case, the reaction pressure is not limited. In a usual case, the product containing the compound (5) has a lower boiling point, and accordingly, it is preferred to obtain it by a method of a reaction distillation system whereby the product is evaporated and continuously withdrawn. Otherwise, a method may be employed wherein after completion of the heating, the product is withdrawn from the reactor all at once. The reaction temperature for this liquid phase heat decomposition reaction is preferably from 50 to 300° C., particularly preferably from 100 to 250° C.

The liquid phase heat decomposition reaction may be carried out in the absence of any solvent or in the presence of a solvent. As such a solvent, there is no particular restriction so long as it is one which is not reactive with the compound (4) and compatible with the compound (4) and which will not react with the resulting compound (5). Further, as the solvent, it is preferred to select one which is readily separable at the time of purification of the compound (5). As a specific example of the solvent, an inert solvent such as a perfluorotrialkylamine or perfluorodecalin, or chlorotrifluoroethylene oligomer (such as FLON LUBE, trade name) having a high boiling point among e.g. chlorofluorocarbons, is preferred. Further, the amount of the solvent is preferably from 10 to 1000 mass % based on the compound (4).

Further, in a case where the compound (4) is decomposed by reacting it with a nucleophilic or electrophilic agent in the liquid phase, such a reaction may be carried out in the absence of any solvent or in the presence of a solvent. As such a solvent, the same one as the solvent in the liquid phase heat decomposition reaction, may be mentioned. The nucleophilic agent is preferably F$^-$, particularly preferably F$^-$ derived from an alkali metal fluoride. As such an alkali metal fluoride, NaF, NaHF$_2$, KF or CsF may be used, and among them, from the viewpoint of the economical efficiency, NaF is particularly preferred, and from such a viewpoint that the reaction can be carried out at a low temperature, KF is particularly preferred.

In a case where a nucleophilic agent (such as F⁻) is employed, the nucleophilic agent employed at the initial stage of the reaction may be in a catalytic amount or in excess. Namely, the amount of the nucleophilic agent such as F⁻ is preferably from 1 to 500 mol %, particularly preferably from 1 to 100 mol %, especially preferably from 5 to 50 mol %, to the compound (4). The reaction temperature is preferably within a range of from −30° C. to the boiling point of the solvent or the compound (4), particularly preferably from −20° C. to 250° C. This method is also preferably carried out in a reaction distillation system.

A decomposition reaction of the ester bond, a —COF group and a $R^{1F}CO$— group will be formed. The group corresponding to the $-E^{F1}$ group may be a —COF group or a $R^{1F}CO$— group. However, in a case where it is led to a polymerizable unsaturated double bond by the thermal decomposition reaction which will be described hereinafter, it is preferably a —COF group. Such a —COF group may be a $R^{1F}CO$— group wherein $R^{1F}$ is a fluorine atom.

The compound (5) is preferably a compound (5-1) which will be formed by the decomposition reaction of the ester bond of the compound (4-1).

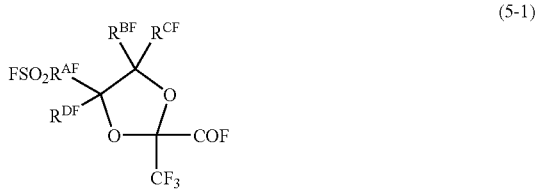

(5-1)

By the decomposition reaction of the ester bond of the compound (4), the following compound (6) will be formed together with the compound (5). Here, $R^{EF}$ has the same meaning as above, and $E^{F2}$ represents a group which will be formed together with $E^{F1}$ formed by scission of $E^F$.

(6)

From the decomposition reaction product of the ester bond, only the compound (5) may be obtained, or both the compound (5) and the compound (6) may be obtained.

In a case where $E^F$ is —COOCFR$^{1F}$—, the group corresponding to $E^{F2}$ is a —COF group or a $R^{1F}CO$— group, and in a case where $R^{1F}$ is a fluorine atom, $E^{F2}$ will be a —COF group irrespective of the direction of $E^F$. In the present invention, each of $E^{F1}$ and $E^{F2}$ is preferably a —COF group. Namely, the compound (5) wherein $E^{F1}$ is a —COF group, is led to a useful compound by the after-mentioned reaction, and the compound (6) wherein $E^{F2}$ is a —COF group, is preferred from such a viewpoint that the after-mentioned continuous reaction can be carried out. Namely, as the compound (6), the following compound (6-1) is preferred.

(6-1)

In the method A, the compound (6-1) is used as the compound (A2-1) to be reacted with the compound (A1-1), whereby it is possible to carry out continuous production of the compound (5-1).

The compound (5-1) can further be led to a polymerizable compound (7-1) by a thermal decomposition reaction. The symbols in the following formula have the same meanings as above.

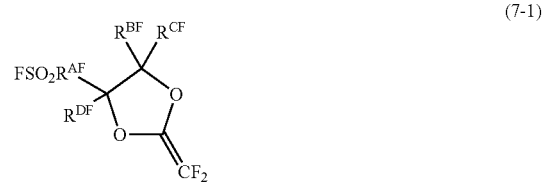

(7-1)

The thermal decomposition reaction can be carried out by a gas phase reaction or a liquid phase reaction, and it is preferably carried out by a gas phase reaction, which is efficient. And, the method for the thermal decomposition reaction and the reaction temperature are preferably selected from the boiling point and the stability of the compound (5-1). Further, the compound (5-1) preferably has a boiling point of at most 350° C. under atmospheric pressure for such a reason that the thermal decomposition reaction can be efficiently carried out in a gas phase reaction. Further, the boiling point of the compound (5-1) is preferably at least 50° C. Further, the gas phase reaction is preferably carried out in the presence of glass beads, an alkali metal salt or an alkaline earth metal salt.

The gas phase reaction is preferably carried out by a continuous reaction. The continuous reaction is preferably carried out by a method wherein the vaporized compound (5-1) is passed through a heated reaction tube, and the formed compound (7-1) is obtained as a discharge gas, and this gas is condensed and continuously recovered.

The reaction temperature in a case where the thermal decomposition is carried out by a gas phase reaction, may optionally be changed depending upon the structure of the compound (5-1). However, it is usually preferably at least 150° C., particularly preferably from 200° C. to 500° C., especially preferably from 250° C. to 450° C. If the reaction temperature is too high, the yield is likely to decrease by a decomposition reaction of the products.

Further, in a case where the thermal decomposition reaction is carried out by a gas phase reaction, it is preferred to employ a tubular reactor. The retention time in a case where a tubular reactor is employed, is preferably at a level of from 0.1 second to 10 minutes on the vacant column basis. The reaction pressure is not particularly limited. In a case where the compound (5-1) is a high boiling point compound, it is preferred that the reaction is carried out under reduced pressure. Especially when the compound (5-1) is a low boiling point compound, the reaction is preferably carried out under an elevated pressure, whereby decomposition of the product can be suppressed, and the conversion will be high.

In a case where the gas phase reaction is carried out by means of a tubular reactor, it is preferred to pack the reaction tube with glass, an alkali metal salt or an alkaline earth metal salt for the purpose of accelerating the reaction. As the alkali metal salt or the alkaline earth metal salt, a carbonate or a fluoride is preferred. The glass may, for example, be a common soda glass, and particularly preferred is glass beads having the fluidity improved in the form of beads. The alkali metal salt may, for example, be sodium carbonate, sodium fluoride, potassium carbonate or lithium carbonate. The alkaline earth metal salt may, for example be calcium carbonate, calcium fluoride or magnesium carbonate. Further, in a case where glass, an alkali metal salt or an alkaline earth metal salt is packed into the reaction tube, it is particularly preferred to use glass beads or light ash of sodium carbonate having a particle size of from about 100 to 250 µm, whereby a reaction system of a fluidized bed type can be employed.

In the gas phase reaction, it is preferred to carry out the reaction in the presence of an inert gas which is not directly concerned with the thermal decomposition reaction, for the purpose of accelerating the vaporization of the compound (5-1). As such an inert gas, nitrogen, carbon dioxide, helium or argon may, for example, be mentioned. The amount of the inert gas is preferably at a level of from 0.01 to 50 vol % based on the compound (5-1). If the amount of the inert gas is too much, the recovery rate of the product tends to be low, such being undesirable. On the other hand, if the boiling point of the compound (5-1) is high, the thermal decomposition may be carried out by a liquid phase reaction.

The thermal decomposition reaction may also be carried out in such a manner that after converting the compound (5-1) to the corresponding alkali metal or alkaline earth metal salt of a carboxylic acid, the thermal decomposition is carried out. In such a method, the compound (5-1) is reacted with an alkali metal or an alkaline earth metal carbonate or hydrogen carbonate, and by removal of the solvent, is led to the corresponding alkali metal or alkaline earth metal salt of a carboxylic acid. By such a method, without hydrolyzing the $FSO_2$— group in the compound (5-1), the —COF group can selectively be led to a salt of a carboxylic acid. The alkali metal carbonate may, for example, be sodium carbonate, potassium carbonate or lithium carbonate. The alkaline earth metal carbonate may, for example, be calcium carbonate or magnesium carbonate. Further, the alkali metal hydrogen carbonate may specifically be sodium hydrogen carbonate, potassium hydrogen carbonate or lithium hydrogen carbonate. The alkaline earth metal hydrogen carbonate may, for example, be calcium hydrogen carbonate or magnesium hydrogen carbonate. Further, the alkali metal or the alkaline earth metal salt to be used is preferably one sufficiently dried. Further, the solvent may be a non-polar solvent or a polar solvent, and it is preferably a polar solvent, since the reaction at a low temperature will thereby be possible. As an example of such a polar solvent, 1,2-dimethoxyethane, diethylene glycol dimethyl ether, tetraethylene glycol dimethyl ether or tetrahydrofuran may, for example, be mentioned.

The temperature for the thermal decomposition of the alkali metal salt of the compound (5-1) is preferably from 100 to 300° C., particularly preferably from 150 to 250° C. The thermal decomposition reaction via an alkali metal salt is preferred since it can be carried out at a relatively low temperature as compared with the gas phase thermal decomposition method.

As the compound (7-1), a compound represented by the following formula (7-1A) is preferred. Here, $R^{AF10}$ represents a $C_{1-20}$ perfluoroalkylene group or a $C_{1-20}$ perfluoro (etheric oxygen atom-containing alkylene) group.

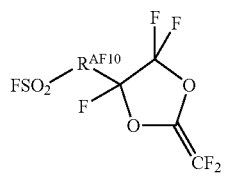

(7-1A)

The compound (7-1) is a compound having a characteristic structure having a polymerizable unsaturated group ($>C=CF_2$) and a fluorosulfonyl group ($FSO_2$— group). A polymer obtained by polymerizing such a compound, is useful for electrolysis of sodium chloride or as an electrolyte material for a fuel cell.

For example, a fluorosulfonyl group-containing polymer formed by homopolymerization of the compound (7-1), is useful as a precursor for a sulfonic polymer having a high molecular weight and a high ion exchange capacity. Further, the compound (7-1) may be copolymerized with another polymerizable monomer (hereinafter referred to as a comonomer) which can be copolymerized with the compound (7-1), to form a fluorosulfonyl group-containing polymer. As such a comonomer, one type or two or more types may be used.

Examples of such a comonomer include, for example, tetrafluoroethylene, chlorotrifluoroethylene, trifluoroethylene, vinylidene fluoride, vinyl fluoride, ethylene, perfluoro (3-butenyl vinyl ether), perfluoro(allyl vinyl ether), perfluoro(2,2-dimethyl-1,3-dioxol), perfluoro(1,3-dioxol), perfluoro(2-methylene-4-methyl-1,3-dioxolane), perfluoro (3,5-dioxa-1,6-heptadiene) and perfluoro(4-methoxy-1,3-dioxol).

Further, as a comonomer, together with the above exemplified comonomer, a perfluoro(α-olefin) such as propene or hexafluoropropene, a (perfluoroalkyl)ethylene such as (perfluorobutyl)ethylene, a (perfluoroalkyl)propene such as 3-perfluorooctyl-1-propene, a perfluorovinyl ether (such as a perfluoro(alkyl vinyl ether), or a perfluoro(etheric oxygen atom-containing alkyl)vinyl ether)), or the like may be used.

The polymerization reaction is not particularly limited so long as it can be carried out under a condition where radicals will be formed. For example, it can be carried out by bulk polymerization, solution polymerization, suspension polymerization, emulsion polymerization, polymerization in a liquid or super critical carbon dioxide, or the like.

The method for generating radicals is not particularly limited. For example, a method of irradiating radiation such as ultraviolet rays, γ-rays or electron rays may be employed, or a method of using a radical initiator which is commonly used for radical polymerization, may be employed. The reaction temperature for polymerization reaction is also not particularly limited. For example, it is usually at a level of from 15 to 150° C. In a case where a radical initiator is used, such a radical initiator may, for example, be a bis(fluoroacyl) peroxide, a bis(chlorofluoroacyl)peroxide, a dialkylperoxy dicarbonate, a diacyl peroxide, a peroxyester, an azo compound or a persulfate.

When solution polymerization is carried out, the solvent to be used preferably has a boiling point of from 20 to 350° C., more preferably from 40 to 150° C., from the viewpoint of handling efficiency.

The molecular weight of the polymer comprising monomer units having the compound (7-1) polymerized is preferably from $5 \times 10^3$ to $5 \times 10^6$, particularly preferably from $1 \times 10^4$ to $3 \times 10^6$. Further, in a case where the polymer containing monomer units having the compound (7-1) polymerized, is a copolymer comprising monomer units having a comonomer polymerized, the proportion of the monomer units having the compound (7-1) polymerized, is preferably from 0.1 to 99.9 mol %, particularly preferably from 5 to 90 mol %, specifically preferably from 10 to 75 mol %, to the total monomer units in the copolymer.

The copolymer of the compound (7-1) with a comonomer, is useful for electrolysis of sodium chloride or for an application as a precursor of an electrolyte material for e.g. a fuel cell. Further, in a case where such a copolymer is used for electrolysis of hydrochloride or for an application for e.g.

a fuel cell, it is preferred to select it from perfluoro compounds, in view of the durability.

As such a comonomer for a perfluoro(alkyl vinyl ether), the following compound (7B) is preferred.

$$CF_2=CF—(OCF_2CFZ)_t—O—R^f \qquad (7B)$$

In the above formula, t is an integer of from 0 to 3, Z is a fluorine atom or a trifluoromethyl group, and $R^f$ is a $C_{1-12}$ perfloroalkyl group. Further, $R^f$ may have a linear structure or a branched structure.

As the perfluorovinyl ether compound (7B), the following compound (7B-1), the following compound (7B-2) or the following compound (7B-3) is preferred. In these formulae, v is an integer of from 1 to 9, w is an integer of from 1 to 9, and x is 2 or 3.

$$CF_2=CFO(CF_2)_vCF_3 \qquad (7B-1)$$

$$CF_2=CFOCF_2CF(CF_3)O(CF_2)_wCF_3 \qquad (7B-2)$$

$$CF_2=CF(OCF_2CF(CF_3))_xO(CF_2)_2CF_3 \qquad (7B-3)$$

Further, in the present invention, fluorosulfonyl groups (—$SO_2F$ groups) based on the compound (7-1) may be subjected to alkali hydrolysis or may be subjected to alkali hydrolysis, followed by acid treatment, whereby a polymer containing sulfonate or sulfonic groups can be produced.

As such a polymer, a fluorosulfonic acid-containing polymer comprising monomer units represented by the following formula, or such monomer units and units of another monomer copolymerizable therewith, may be mentioned. In the formula, M represents a hydrogen atom or a counter ion.

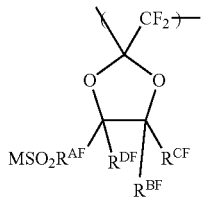

The polymer comprising sulfonate or sulfonic groups preferably has a molecular weight of from $5\times10^3$ to $5\times10^6$, and in a case where it contains monomer units of another copolymerizable monomer, it is preferably a polymer containing such monomer units in an amount of from 0.1 to 99.9 mol %.

In the alkali hydrolysis, it is preferred to use an alkali metal hydroxide or an alkali metal carbonate. In the acid treatment, it is preferred to employ hydrochloric acid, nitric acid or sulfonic acid. Fluorosulfonyl groups will thereby be converted to sulfonate groups (—$SO_3M^1$ groups, wherein $M^1$ is a counter ion). Here, $M^1$ is preferably an alkali metal ion or $N^+R^1R^2R^3R^4$ (wherein each of $R^1$ to $R^4$ which are independent of one another, is a hydrogen atom or a $C_{1-5}$ alkyl group). The alkali metal ion is preferably a sodium ion, a potassium ion or a lithium ion. Further, $N^+R^1R^2R^3R^4$ is preferably $N^+(CH_3)_4$, $N^+(CH_2CH_3)_4$, $N^+(CH_2CH_2CH_3)_4$ or $N_+(CH_2CH_2CH_3)_4$ is preferred.

A polymer wherein $M^1$ in the sulfonate group is an alkali metal ion, is preferably obtained by reacting an alkali metal hydroxide with a sulfonic group-containing polymer. Further, a polymer wherein $M^1$ in the sulfonate group is $N^+R^1R^2R^3R^4$, is preferably obtained by reacting a compound represented by the formula $NR^1R^2R^3R^4(OH)$ with a fluorosulfonyl group-containing polymer.

Further, a polymer comprising sulfonate groups obtained by hydrolysis, may be dipped in an aqueous solution containing ions capable of becoming counter ions different from $M^1$, to change $M^1$ to other counter ions.

Further, sulfonate groups (—$SO_3M^1$ groups) can be converted to sulfonic groups (—$SO_3H$ groups) by treatment with an acid such as hydrochloric acid, nitric acid or sulfonic acid.

Such a method for conversion of the groups can be carried out in accordance with conventional methods and conditions.

The polymer having fluorosulfonyl groups obtained by the process of the present invention is excellent in adhesion to other substrates. Further, it has a high refractive index as compared with a perfluoropolymer having no functional group, it is useful also as an optical material. Further, a polymer comprising sulfonate or sulfonic groups obtained by the process of the present invention can be used not only for electrolysis of sodium chloride or as an electrolyte material for a fuel cell, but also for various applications as a solid electrolyte material.

For example, it can be used for a proton selective permeation membrane to be used for electrolysis of water, production of hydrogen peroxide, production of ozone, recovery of a waste acid, etc., or as a cation exchange membrane for electrodialysis to be used for desalination or salt production. Further, it can be used also as a polymer electrolyte for a lithium ion cell, a solid acid catalyst, a cation exchange resin, a sensor employing a modified electrode, an ion exchange filter to remove a trace amount of ions in air, or an actuator. Namely, the polymer obtained by the polymerization reaction of the compound (7-1) can be used as a material for various electrochemical processes.

Further, a polymer containing sulfonate groups or sulfonic groups can be used also for a membrane for diffuse dialysis to be used for separation and purification of acids, bases and salts, a charged porous membrane for separating proteins (such as a charged reverse osmosis membrane, a charged ultrafiltration membrane, a charged microfiltration membrane, etc.), a dehumidifying membrane, a humidifying membrane, etc.

Further, the following embodiments may be mentioned as preferred embodiments in the present invention.

Namely, a process for producing the following compound (5-10), characterized in that the following compound (3-10) is fluorinated to form the following compound (4-10), and then, the ester bond of the compound (4-10) is decomposed. A process for producing the following compound (7-10), by thermally decomposing the compound (5-10), or converting the compound (5-10) to the following compound (6-10) (wherein $M^2$ is an alkali metal atom ion), followed by thermal decomposition. Further, a polymer comprising monomer units having at least one type of the compound (7-10) polymerized, or monomer units having at least one type of the compound (7-10) polymerized and monomer units formed by polymerizing such a compound with at least one copolymerizable monomer, and a process for its production. Further, a process for producing a sulfonate or sulfonic group-containing polymer, wherein fluorosulfonyl groups in the polymer are subjected to alkali hydrolysis, or such alkali hydrolysis is followed by acid treatment. The following compounds in such processes, are novel compounds.

(3-10)
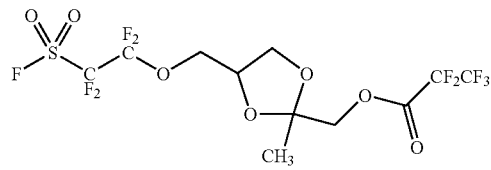

(4-10)
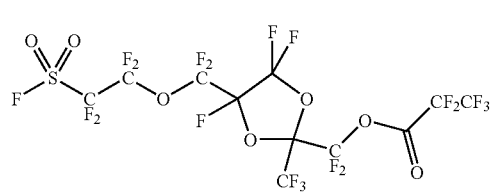

(5-10)
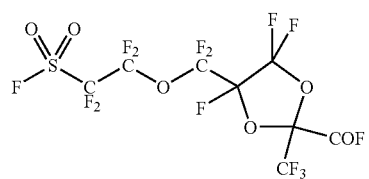

(6-10)
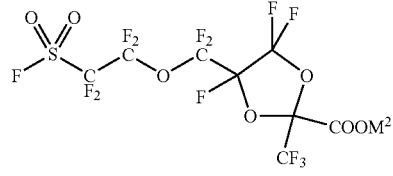

(7-10)
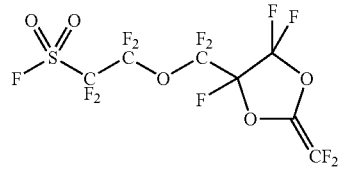

EXAMPLES

Now, the present invention will be described in detail with reference to Examples. However, it should be understood that the present invention is by no means restricted thereto.

In the following, 1,1,2-trichlorotrifluoroethane will be referred to as R-113, $CClF_2CF_2CHClF$ as HCFC225cb, gas chromatography as GC, size exclusion chromatography as GPC, a number average molecular weight as $M_n$, and a weight average molecular weight as $M_w$.

A quantitative determination by means of $^{19}$F-NMR was carried out by using perfluorobenzene as the internal standard. The quantitative determination value by GC is a value obtained from the peak area ratio. For GPC, SEC HLC-8020, name of the apparatus manufactured by TOSOH CORPORATION, was used, as the mobile phase, HCFC225cb/hexafluoroisopropyl alcohol (99/1 volume ratio) was used, two columns of P1gel 5 μ MIXED-C manufactured by Polymer Laboratories Ltd., were used, and as the standard sample for calculation of the molecular weight, methyl polymethacrylate was used.

Example 1

Preparation of Compound (B1-10)

(C1-10)
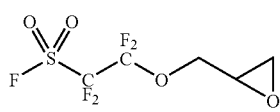

(B1-10)
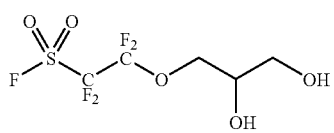

The compound (C1-10) was prepared by the method disclosed in J. Fluorine Chem., Vol. 46, 39 (1990). From the compound (C1-10), the compound (B1-10) was prepared in accordance with the method disclosed in J. Fluorine Chem., Vol. 68, 253 (1994). However, the perfluoroion exchange resin beads (trade name: Nafion NR50) disclosed as a solid acid catalyst in the reference was changed to a 10 to 20% fluorosulfonic acid nanocomposite (trade name: Nafion SAC-13, hereinafter referred by the trade name) supported on amorphous silica. From the compound (C1-10) (105.7 g), the compound (B1-10) (43.5 g) was obtained.

Example 2

Preparation of Compound (B2-10)

$CH_3C(O)CH_2OCOCF_2CF_3$     (B2-10)

$CH_3COCH_2OH$ (150.0 g) and triethylamine (225.4 g) were put into a flask and stirred under cooling in an ice bath. $CF_3CF_2COF$ (377.5 g) diluted with nitrogen gas was blown into the flask over a period of 4 hours, while maintaining the internal temperature to be at most 10° C. Then, the mixture was stirred at room temperature for 2 hours and then added to 500 mL of ice water.

The obtained crude liquid was subjected to liquid separation to obtain a fluorocarbon layer. Further, the fluorocarbon layer was washed twice with water (250 mL) and dried over magnesium sulfate. It was further subjected to filtration to obtain a crude liquid. The filtrate was distilled under reduced pressure to obtain a compound (B2-10) (167.3 g) as a fraction of from 47.1 to 47.9° C./0.7 kPa (absolute pressure). The purity of the fraction by GC was 99%.

$^1$H-NMR (300.4 MHz, solvent: $CDCl_3$, standard: $CHCl_3$) δ (ppm):2.22(s, 3H), 4.92(s, 2H).

$^{19}$F-NMR (282.7 MHz, solvent: $CDCl_3$, standard: $CFCl_3$) δ (ppm):−82.9 (3F), −121.4 (2F).

Example 3

Preparation of Compound (3-10)

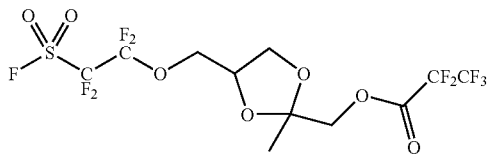
(3-10)

Preparation by Method B

Into a 200 mL flask, the compound (B1-10) (40.0 g) obtained in Example 1, the compound (B2-10) (32.1 g) obtained in Example 2, ethyl orthoformate (21.6 g) and Nafion SAC-13 (2.0 g) were charged and stirred for 4 hours at an internal temperature of 80° C. Then, the interior of the reactor was depressurized to remove a low boiling component thereby to obtain a crude liquid. The crude liquid was purified by silica gel column chromatography (developing solvent: HCFC225cb) to obtain the compound (3-10) (64.3 g). The GC purity was 93%.

Preparation by Method C

In a dry atmosphere, boron trifluoride etherate (32.01 g) and dehydrated acetone (4.5 L) were mixed, and the compound (C1-10) (1198.1 g) obtained in Example 1 and diluted with dehydrated acetone (1.2 L), was dropwise added to the above mixture, followed by heating and refluxing for one hour to obtain the compound (C1-20). After distilling off about a half of the acetone, the compound (B2-10) (1031.41 g) obtained in Example 2 was diluted with toluene (2 L) and added to the reaction system. While heating at a temperature of at most 65° C., the rest of acetone was distilled off under reduced pressure. The reaction mixture was poured into a mixture of a saturated sodium hydrogen carbonate aqueous solution and ice, and extracted three times with t-butyl methyl ether (2.9 L), and the extract solution was dried over magnesium sulfate, the drying agent was removed by filtration under reduced pressure, and the filtrate was concentrated. The residue was purified by silica gel column chromatography (developing solvent: HCFC225cb/n-hexane=1:1, and then only HCFC225cb) to obtain the compound (3-10) (1478.95 g). The GC purity was 99%.

$^1$H-NMR (300.4 MHz, solvent: CDCl$_3$, standard: CHCl$_3$) δ (ppm):1.42, 1.45(s, 3H), 3.82-3.93(m, 1H), 4.11-4.25 (m, 4H), 4.35-4.46 (m, 2H).

$^{19}$F-NMR (282.7 MHz, solvent: CDCl$_3$, standard: CFCl$_3$) δ (ppm):43.3 (1F), −82.9 (3F), −84.1 (2F), −110.9 (2F), −121.4 (2F).

Example 4

Preparation of Compound (4-10)

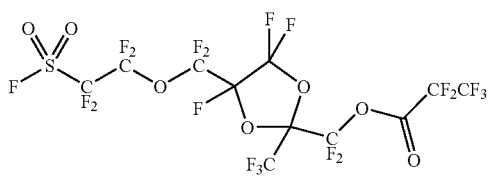
(4-10)

Into a 500 mL autoclave made of nickel, R-113 (312 g) was added, stirred and maintained at 25° C. At the gas outlet of the autoclave, a cooler maintained at 20° C., NaF pellets packing layer, and a cooler maintained at −10° C., were installed in series. A liquid returning line was installed to return the condensed liquid from the cooler to the autoclave.

After blowing a nitrogen gas for 1.0 hour, a fluorine gas diluted with nitrogen gas to 20% (hereinafter referred to as a diluted fluorine gas) was blown thereinto at a flow rate of 12.72 L/hr for one hour. Then, while blowing the fluorine gas at the same flow rate, a solution having the compound (3-10)(20.0 g) obtained in Example 3, dissolved in R-113 (200 g), was injected over a period of 7.6 hours.

Then, while blowing the diluted fluorine gas at the same flow rate and maintaining the pressure of the reactor at 0.15 MPa, a R-113 solution having a benzene concentration of 0.01 g/ml was injected in an amount of 23 mL while raising the temperature from 25° C. to 40° C. Further, the benzene inlet of the autoclave was closed, and stirring was continued for 1.0 hour while maintaining the pressure of the reactor at 0.15 MPa and the internal temperature of the reactor at 40° C. The total amount of benzene injected was 0.22 g, and the total amount of R-113 injected was 23 mL. Further, nitrogen gas was blown thereinto for 1.0 hour. The product was analyzed by $^{19}$F-NMR, whereby formation of the above identified compound was confirmed, and the yield was 98%.

$^{19}$F-NMR (376.0 MHz, solvent: CDCl$_3$, standard: CFCl$_3$) δ (ppm):45.3 (1F), −77.4 (1F), −80.1 (3F), −80.7 to −81.4 (1F), −82.1 (1F), −82.5 (2F), −83.3 (3F), −82.7 to −83.6 (1F), −85.5 to −87.1 (2F), −112.8 (2F), −121.9 (1F), −122.2 (2F).

Example 5

Preparation of Compound (5-10) by a Liquid Phase Thermal Decomposition Reaction

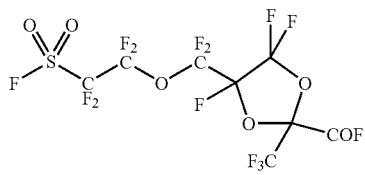
(5-10)

Example 5-1

The compound (4-10) (10.6 g) obtained in Example 4 was together with sufficiently dried KF powder (0.18 g) charged into a flask and stirred at room temperature for 24 hours. After cooling, a sample (8.8 g) recovered from the flask was subjected to filtration to recover a liquid sample. By NMR and GC-MS, the main product was confirmed to be the above identified compound. The yield was 77.8%.

$^{19}$F-NMR (282.7 MHz, solvent: CDCl$_3$, standard: CFCl$_3$) δ (ppm):45.5 (1F), 24.4 (1F), −77.9 to −79.1 (1F), −81.7 (3F), −81.9 to −82.4 (3F), −82.8 to −83.9 (2F), −112.7 (2F), −123.5 to −124.7 (1F).

Example 5-2

In the same manner as in Example 5-1, a reaction solution (531 g) containing the compound (5-10) as the main component, was obtained from the compound (4-10) (706 g). The reaction solution was subjected to distillation under reduced pressure to obtain the compound (5-10) (481 g) having a purity of 99%. The temperature for distillation was from 71 to 73° C./5.3 kPa.

Example 6

Preparation of Compound (7-10) and Compound (7-2)

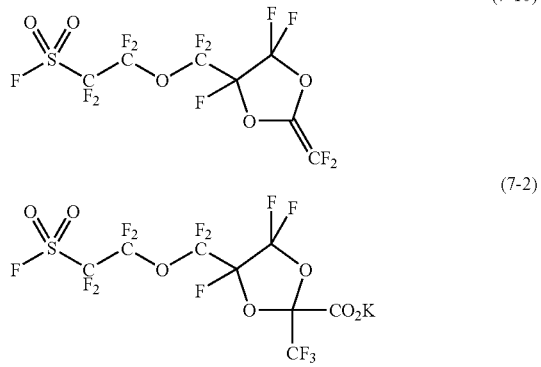

Example 6-1

Into a 100 mL three-necked flask, potassium hydrogen carbonate (3.21 g, 0.032 mol) and 1,2-dimethoxyethane (24.4 g) were charged. Then, the flask was cooled until the internal temperature became from 5 to 10° C., and the compound (5-10) (15.4 g, 0.0314 mol) was dropwise added with stirring sufficiently. During the dropwise addition, the internal temperature of the flask was maintained to be from 5 to 20° C. The mixture was further stirred at room temperature. Then, 1,2-dimethoxyethane was distilled off under reduced pressure, and a formed solid was pulverized and dried for two days at from 80 to 100° C. by means of a reduced pressure dryer to obtain the compound (7-2) (13.9 g, 0.0264 mol).

Then, into 100 mL three necked flask, the compound (7-2) (12.9 g, 0.0245 mol) was charged and heated until the internal temperature became from 190 to 200° C. under vacuum to carry out a thermal decomposition reaction. The product was recovered by a dry ice trap on the vacuum pump side. Further, the crude product was distilled to obtain the compound (7-10) (1.47 g).

Precise mass (EI) 423.9263 (M+H) [theoretical value: $C_7O_5F_{12}S$=423.9275].

$^{19}$F-NMR (564.55 MHz, solvent: CDCl$_3$, standard: CFCl$_3$) δ (ppm):45.3 (1F), −82.0 to −83.7 (5F), −87.7 (1F), −112.8 (2F), −125.2 (1F), −126.5 (1F), −128.4 (1F).

Example 6-2

A stainless steel reaction tube (a fluidized bed type) having an inner diameter of ½ inch packed with glass beads, was heated to 350° C., and a gas mixture of the compound (5-10) and nitrogen (molar ratio of 1:9) preliminarily heated to the same temperature was passed through. The retention time was 10 seconds, and the linear velocity was 2.5 cm/sec. The amount of the compound (5-10) used, was 68.1 g. By cooling the gas discharged from the reaction tube, a liquid containing the compound (7-10) as the main component, was obtained. The yield of the reaction was 52%.

Then, methanol was added to the reaction solution, and an unreacted compound (5-10) was methyl esterified. Washing with water was followed by distillation to obtain a purified compound (5-10).

The boiling point was 48° C./2.7 kPa.

Example 7

Preparation of Homopolymer of Compound (7-10)

The compound (7-10) (1.25 g) obtained in Example 6-1 and perfluorobenzoyl peroxide (4.5 mg) were put into a glass tube and frozen with liquid nitrogen, followed by sealing under vacuum. After maintaining the glass tube at 70° C. for 45 hours, the formed polymer was taken out and dissolved in n-C$_6$F$_{13}$H, reprecipitated by hexane, followed by washing and dried under reduced pressure at 80° C. for 16 hours. The data of $^{19}$FNMR (282.65 MHz, solvent: benzene-d$_6$ was added to perfluorobenzene, standard: CFCl$_3$) are shown in FIG. 1. At 46.0 ppm, a signal of a fluorine atom of 1F derived from —SO$_2$F was confirmed. The obtained amount of the homopolymer of the compound (7-10) was 0.823 g (yield: 66%). $M_n$ by GPC was 6.5×10$^4$, and $M_w$ was 9.8×10$^4$. The glass transition temperature measured by DSC, was 92° C.

Further, reprecipitation and washing were carried out, and a low boiling point component was distilled off under reduced pressure. Further, as a result of drying under reduced pressure at 80° C. for 16 hours, a powdery polymer (0.072 g) made of the above-identified polymer was recovered. The yield obtained by adding to the previously obtained polymer was 71%.

Example 8

Production of Copolymer of Compound (7-10) with Perfluoro(2-Methylene-4-Methyl-1,3-Dioxolane)

Into a stainless steel autoclave having a capacity of 0.1 L, the compound (7-10) (7.9 g), perfluoro(2-methylene-4-methyl-1,3-dioxolane) (9.6 g), HCFC225cb (109.7 g) and perfluorobenzoyl peroxide (255 mg) were charged and cooled with liquid nitrogen for deaeration. The mixture was reacted at 70° C. for 5 hours and then put into hexane to precipitate the polymer. The polymer was washed with hexane and then vacuum-dried at 100° C. to obtain 14.0 g of a white polymer. From the content of sulfur obtained by the elemental analysis, the composition of the obtained polymer was such that the compound (7-10)/perfluoro(2-methylene-4-methyl-1,3-dioxolane)=34.6/65.4 (molar ratio). The specific viscosity at 30° C. measured by using perfluoro(2-butyltetrahydrofuran) as a solvent, was 0.16 dl/g.

To the obtained copolymer (10 g), methanol (40 g) and a 10% KOH aqueous solution (160 g) were added, and the mixture was held at 60° C. for one week to convert fluorosulfonyl groups in the copolymer to a potassium salt of sulfonic acid. After filtration, the copolymer was immersed in ion-exchanged water and held overnight at 60° C. This operation of filtration and immersion in water was repeated three times. After filtration, the copolymer was immersed overnight at 60° C. in 1 mol/L hydrochloric acid. This operation of filtration and immersion in hydrochloric acid was repeated four times. Then, the same operation of filtration and immersion in water as above, was repeated three times. After confirming that the filtrate was neutral, the copolymer was dried overnight in an oven of 80° C. in air and then further vacuum dried overnight at 80° C. to obtain a sulfonic group-containing copolymer.

Example 9

Preparation of Copolymer of Compound (7-10) with Tetrafluoroethylene

Into a stainless steel autoclave having a capacity of 0.1 L, the compound (7-10) (8.48 g), HCFC225cb (76.3 g) containing 17 mg of methanol, and perfluorobenzoyl peroxide (170 mg) were charged and cooled with liquid nitrogen for deaeration. After introducing tetrafluoroethylene (11.3 g), a reaction was carried out at 70° C. for 50 minutes. During this period, the gauge pressure decreased from 0.97 MPa to 0.43 MPa. After cooling, the gas in the system was purged, and the reaction mixture was put into hexane to precipitate a polymer. The polymer was washed with hexane and then vacuum-dried at 100° C. to obtain a white polymer (14.1 g) The composition of the polymer obtained from the content of sulfur as determined by the elemental analysis, was such that the compound (7-10)/tetrafluoroethylene=17.6/82.4 (molar ratio).

Then, the volume flow rate of the obtained polymer was measured. In the present invention, the volume flow rate is the extruded amount when melt extrusion of the resin is carried out under an extrusion pressure condition of 30 kg/cm$^2$ by using a nozzle having a length of 1 mm and an inner diameter of 1 mm, and its unit is mm$^3$/sec. The volume flow rate at 300° C. of the copolymer of the present invention was measured by using flow tester CFT-500A (manufactured by Shimadzu Corporation) and found to be 34 mm$^3$/sec.

The copolymer of this example was pressed at 300° C. to obtain a film having a thickness of about 100 μm. This film was immersed at 90° C. for 16 hours in a liquid comprising 30% of DMSO, 11% of KOH and 59% of water to convert fluorosulfonyl groups to a potassium salt of sulfonic acid. After washing with water, the film was immersed in 1 mol/L sulfuric acid, followed by washing with water, to convert it to a film made of a sulfonic group-containing copolymer.

Comparative Example

CF$_2$=CFOCF$_2$CF(CF$_3$)OCF$_2$CF$_2$SO$_2$F (1.25 g) and perfluorobenzoyl peroxide (4.5 mg) were put in a glass tube and frozen by liquid nitrogen, and then, the glass tube was sealed under vacuum. Even after the reaction at 70° C. for 45 hours, the reaction solution stayed to be a colorless transparent liquid. The reaction solution was transferred to a round-bottomed flask, the glass tube wall was washed with HCFC225cb, and the washed liquid was added to the above round-bottomed flask. Under reduced pressure, a low boiling point component was distilled off, followed by drying under reduced pressure at 80° C. for 16 hours, to obtain a starch syrup-like oligomer (0.328 g). The polymer yield was 26%. Mn by GPC was 3.7×10$^3$, M$_w$ was 4.7×10$^3$.

INDUSTRIAL APPLICABILITY

According to the process of the present invention, it is possible to efficiently produce a compound useful for an ion exchange membrane, particularly a membrane for electrolysis of sodium chloride or for a solid polymer type fuel cell, or as an electrolyte to be used for the catalyst layer of such a fuel cell, or as a starting material thereof, in a short process from a readily available compound.

Further, according to the present invention, a polymer, etc. to be used for the above application, or a novel compound useful as a starting material therefore, can be presented.

The entire disclosure of Japanese Patent Application No. 2001-332813 filed on Oct. 30, 2001 including specification, claims, drawings and summary is incorporated herein by reference in its entirety.

What is claimed is:

1. A process for producing a fluorosulfonyl group-containing polymer, comprising:
   polymerizing at least one member of compound (7-1), or
   polymerizing at least one member of compound (7-1) and at least one member of a polymerizable monomer which is copolymerizable with compound (7-1):

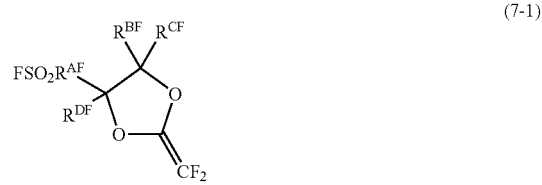

(7-1)

wherein:
   $R^{AF}$ is a bivalent organic group
   $R^{BF}$, $R^{CF}$ and $R^{DF}$ are, independently, a hydrogen atom, a halogen atom or a monovalent organic group.

2. A process for producing a sulfonate or sulfonic group-containing polymer, comprising:
   subjecting to alkali hydrolysis fluorosulfonyl groups of the fluorosulfonyl group-containing polymer produced by the process of claim 1,
   optionally followed by acid treatment.

3. A fluorosulfonyl group-containing polymer, comprising:
   polymerized monomer units of at least one member of compound (7-1), or
   polymerized monomer units of at least one member of compound (7-1) and monomer units of at least one member of a polymerizable monomer which is copolymerizable with compound (7-1), wherein compound (7-1) is:

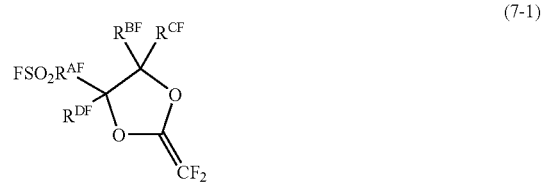

(7-1)

wherein:
   $R^{AF}$ is a bivalent organic group
   $R^{BF}$, $R^{CF}$ and $R^{DF}$ are, independently, a hydrogen atom, a halogen atom or a monovalent organic group.

4. The fluorosulfonyl group-containing polymer according to claim 3, which has an average molecular weight of from 5×10$^3$ to 5×10$^6$ and contains from 0.1 to 99.9 mol % of the monomer units having polymerized at least one member of a polymerizable monomer which is copolymerizable with compound (7-1).

5. A fluorosulfonic group-containing polymer comprising: monomer units represented by the following formula, or such monomer units and monomer units of another monomer which is copolymerizable with such monomer units:

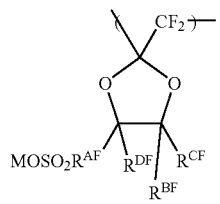

wherein M is a hydrogen atom or a counter ion, wherein $R^{AF}$ is a bivalent organic group
$R^{BF}$, $R^{CF}$ and $R^{DF}$ are, independently, a hydrogen atom, a halogen atom or a monovalent organic group.

6. The fluorosulfonic group-containing polymer according to claim 5, which has an average molecular weight of from $5\times10^3$ to $5\times10^6$ and contains from 0.1 to 99.9 mol % of the monomer units of another copolymerizable monomer.

7. A compound represented by the following formula (7-1A):

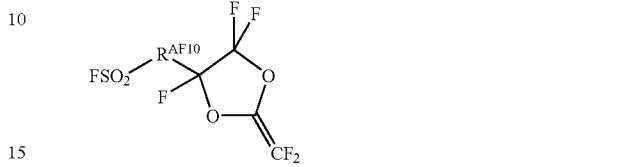

(7-1A)

wherein $R^{AF10}$ is a $C_{1-20}$ perfluoroalkylene group or a $C_{1-20}$ perfluoro(etheric oxygen atom-containing alkylene) group.

* * * * *